(12) United States Patent
Ayala et al.

(10) Patent No.: US 7,758,592 B2
(45) Date of Patent: Jul. 20, 2010

(54) LOOP TIP WIRE GUIDE

(75) Inventors: Juan Carlos Ayala, Santiago (CL); David M. Hardin, Winston-Salem, NC (US); Jason D. Foushee, Durham, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 1241 days.

(21) Appl. No.: 11/234,992

(22) Filed: Sep. 26, 2005

(65) Prior Publication Data

US 2006/0100545 A1 May 11, 2006

Related U.S. Application Data

(63) Continuation-in-part of application No. 10/719,764, filed on Nov. 21, 2003, now Pat. No. 7,520,881.

(60) Provisional application No. 60/614,756, filed on Sep. 30, 2004, provisional application No. 60/430,466, filed on Dec. 2, 2002.

(51) Int. Cl.
*A61B 17/24* (2006.01)
(52) U.S. Cl. ..................................... 606/113
(58) Field of Classification Search ................. 606/113, 606/114, 127, 159, 200; 600/434, 585
See application file for complete search history.

(56) References Cited

U.S. PATENT DOCUMENTS

| 4,281,660 | A | 8/1981 | Fujiwara | 600/375 |
|---|---|---|---|---|
| 4,310,789 | A | 1/1982 | Mank et al. | 318/587 |
| 4,545,390 | A | 10/1985 | Leary | 600/462 |
| 4,800,890 | A | 1/1989 | Cramer | 600/434 |
| 5,037,391 | A | 8/1991 | Hammerslag et al. | 604/528 |
| 5,054,501 | A | 10/1991 | Chuttani et al. | 600/585 |
| 5,069,217 | A | 12/1991 | Fleischhacker, Jr. | 600/585 |
| 5,211,636 | A | 5/1993 | Mische | 604/264 |
| 5,376,083 | A | 12/1994 | Mische | 604/264 |
| 5,387,219 | A | 2/1995 | Rappe | 606/108 |
| 5,433,200 | A | 7/1995 | Fleischhacker, Jr. | 600/434 |
| 5,490,845 | A | 2/1996 | Racz | 604/266 |

(Continued)

FOREIGN PATENT DOCUMENTS

EP 1 346 747 A 9/2003

(Continued)

OTHER PUBLICATIONS

International Search Report dated Jan. 17, 2006 for corresponding International Application No. PCT/US2005/034280.

(Continued)

*Primary Examiner*—Kevin T Truong
(74) *Attorney, Agent, or Firm*—Brinks Hofer Gilson & Lione

(57) ABSTRACT

A wire guide has first and second portions with first and second diameters, respectively. A resilient loop positions a distal end of the wire guide adjacent another section of the wire guide. A closure member comprising at least one attachment tab maintains the distal end in a fixed position relative to the remainder of the wire guide. A covering may be positioned around one or more parts of the wire guide.

16 Claims, 4 Drawing Sheets

U.S. PATENT DOCUMENTS

| | | | |
|---|---|---|---|
| 5,498,249 A | 3/1996 | Quinn | 604/528 |
| 5,613,973 A | 3/1997 | Jackson et al. | 606/113 |
| 5,643,281 A | 7/1997 | Suhocki et al. | 606/113 |
| 5,728,122 A | 3/1998 | Leschinsky et al. | 606/213 |
| 5,730,704 A | 3/1998 | Avitall | 600/374 |
| 5,824,031 A | 10/1998 | Cookston et al. | 607/122 |
| 5,868,754 A * | 2/1999 | Levine et al. | 606/108 |
| 5,904,648 A | 5/1999 | Arndt et al. | 600/120 |
| 6,056,743 A | 5/2000 | Ellis et al. | 606/15 |
| 6,102,918 A | 8/2000 | Kerr | 606/108 |
| 6,277,139 B1 | 8/2001 | Levinson et al. | 606/200 |
| 6,371,970 B1 | 4/2002 | Khosravi et al. | 606/200 |
| 6,379,319 B1 | 4/2002 | Garibotto et al. | 600/585 |
| 6,454,758 B1 | 9/2002 | Thompson et al. | 604/528 |
| 6,464,699 B1 | 10/2002 | Swanson | 606/41 |
| 6,620,179 B2 | 9/2003 | Boock et al. | 606/159 |
| 7,520,881 B2 * | 4/2009 | Foushee et al. | 606/113 |
| 2002/0010426 A1 | 1/2002 | Clayman et al. | 604/170.01 |
| 2002/0016604 A1 | 2/2002 | Boock et al. | 606/159 |
| 2004/0016849 A1 | 1/2004 | Jakubowski et al. | 244/137.4 |
| 2004/0082881 A1 | 4/2004 | Grewe et al. | 600/585 |
| 2004/0106897 A1 | 6/2004 | Thompson et al. | 604/95.04 |
| 2004/0125139 A1 | 7/2004 | Beck et al. | 345/764 |
| 2004/0193032 A1 | 9/2004 | Mogul | 600/374 |
| 2004/0193205 A1 | 9/2004 | Burgermeister | 606/194 |
| 2004/0215208 A1 | 10/2004 | Foushee et al. | 606/108 |
| 2005/0027243 A1 | 2/2005 | Gibson et al. | 604/95.04 |
| 2005/0038412 A1 | 2/2005 | Rabiner et al. | 604/528 |
| 2005/0043779 A1 | 2/2005 | Wilson | 623/1.11 |
| 2005/0080356 A1 | 4/2005 | Dapolito et al. | 600/585 |
| 2005/0096590 A1 | 5/2005 | Gullickson et al. | 604/95.04 |
| 2006/0100544 A1 | 5/2006 | Ayala et al. | 600/585 |

FOREIGN PATENT DOCUMENTS

| | | |
|---|---|---|
| JP | 07088191 | 4/1995 |
| JP | 2001-046508 | 2/2001 |
| WO | WO 00/65987 | 11/2000 |
| WO | WO 2004/050161 A | 6/2004 |
| WO | WO 2004/089456 A | 10/2004 |

OTHER PUBLICATIONS

Office Action issued by the JPO in related Japanese Patent Application 2004-557259, filed Nov. 21, 2003.

* cited by examiner

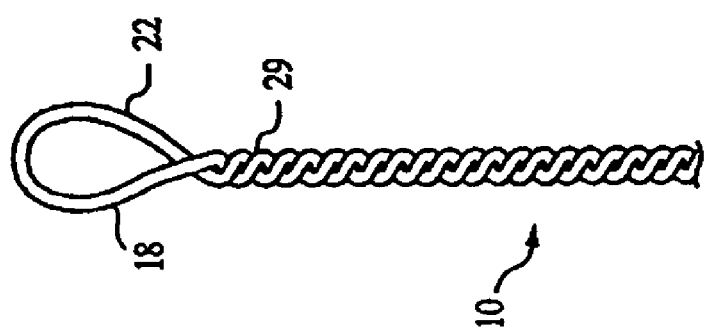
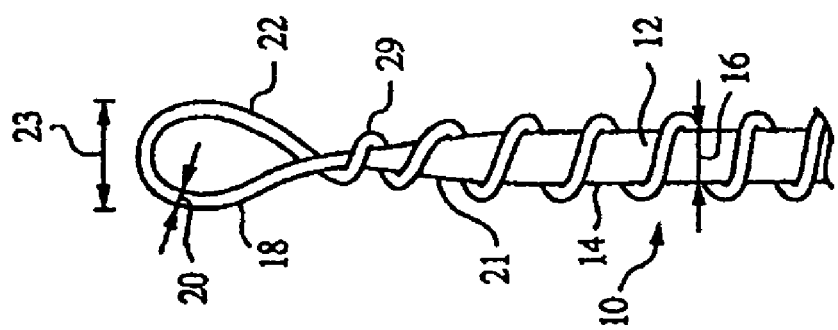

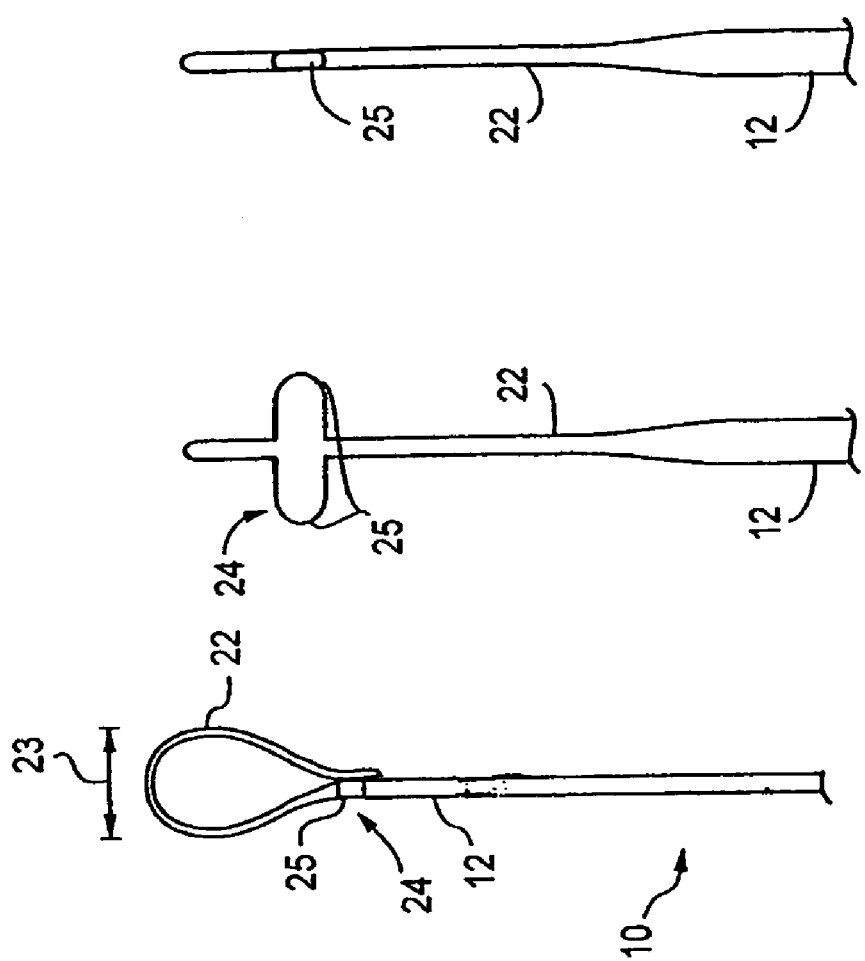

LOOP TIP WIRE GUIDE

RELATED APPLICATIONS

This application claims priority from U.S. Provisional Application No. 60/614,756, filed Sep. 30, 2004, which is incorporated herein by reference. This application is a continuation-in-part of non-provisional application Ser. No. 10/719,764, filed Nov. 21, 2003, now U.S. Pat. No. 7,520,881 which claims priority from U.S. Provisional Application No. 60/430,466, filed Dec. 2, 2002, both of which are incorporated herein by reference.

FIELD OF THE INVENTION

The present invention relates to wire guides used in the placement of medical devices. More specifically, the present invention relates to a wire guide having a loop tip.

BACKGROUND OF THE INVENTION

Wire guides are elongate flexible members used to provide a path along which another medical device can be moved. The path provided by the wire guide can be used to navigate another medical device, such as a catheter, through a body vessel. The use of wire guides to define such a path is known in the art. Briefly, a wire guide is navigated through a body vessel toward a point of treatment. Once positioned within the vessel, a second medical device, frequently a cannula such as a catheter, is placed over the wire guide and moved along its length toward the point of treatment. Thus, the wire guide provides an established path for placing other devices, eliminating the need for performing delicate navigation procedures for each device passed into the vessel.

During placement of a wire guide, an operator must navigate the wire guide through the vessel(s). Often, the vessel defines a torturous path due to the presence of natural bends and/or curves, or unnatural impediments, such as tumors, build-ups, and/or strictures. The presence of a torturous path may make navigation of a wire guide difficult. For example, the presence of an impediment may block the wire guide from navigating further into the vessel.

The prior art contains many examples of wire guides having straight flexible tips intended to aid in the navigation around such impediment. The presence of a straight flexible tip, however, may in fact make navigation more difficult. For example, upon encountering an impediment, the straight flexible tip may bend toward one of the vessel walls, which may result in unintended contact between the tip and vessel wall. This situation may lead to undesirable effects in the vessel wall. Further, the straight tip may bend and turn back upon itself upon encountering the impediment. This formation of an unstable turn in the wire guide makes further navigation difficult.

BRIEF SUMMARY OF THE INVENTION

The present invention provides a wire guide capable of manipulating about a torturous path and/or an impediment. The wire guide comprises a loop at one end. In one embodiment, a wire guide according to the present invention comprises an elongate member having a first portion with a first diameter and a second portion with a second diameter. The second diameter is smaller than the first diameter.

In one embodiment, the elongate member defines a loop. The elongate member is bent back upon itself to form a loop having an interior space. A closure member closes the loop such that the interior space is closed. In one embodiment, the closure member comprises at least one attachment tab, which is bent about a portion of the elongate member.

In one embodiment, the elongate member further comprises an intermediate region defining a taper from the first diameter to the second diameter. Preferably, the loop places a distal end of the wire guide adjacent this intermediate portion. Alternatively, the loop can place the distal end adjacent the second portion.

The second portion can define a portion of the loop, or the entire loop. If present, the intermediate portion can define a portion of the loop.

The loop is resilient and is preferably fixed in overall size. The closure member preferably fixes the distal end relative to another portion of the elongate member. Also preferable, the loop defines a loop width that is greater than the first diameter of the first portion of the elongate member.

In one embodiment, a covering is positioned over at least the closure member. Particularly preferable, the covering is positioned over the closure member and at least the first portion of the elongate member.

BRIEF DESCRIPTION OF THE DRAWINGS

FIG. 11 is a side view of a wire guide according to a ninth embodiment of the invention.

FIG. 12 is a side view of a wire guide according to a tenth embodiment of the invention.

FIG. 13 is a side view of a wire guide according to an eleventh embodiment of the invention.

FIG. 14 is a top-view of the steerable wire-guide of FIG. 13 in an unassembled form illustrating an alternate embodiment of a closure member.

FIG. 15 is a side-view of the steerable wire-guide of FIG. 13.

DETAILED DESCRIPTION OF THE INVENTION

Figure 1:
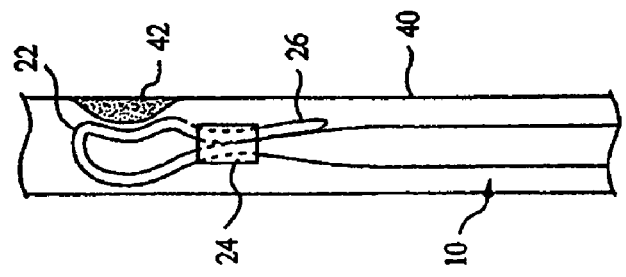
FIG. 1 is a side view of a wire guide according to a first embodiment of the invention.

FIG. 1 illustrates a wire guide 10 according to a first embodiment of the present invention. The wire guide comprises an elongate member 12 having a first portion 14 with a first diameter 16 and a second portion 18 with a second diameter 20. The second diameter 20 is smaller than the first diameter 16. The elongate member 12 has an intermediate portion 21 that defines a taper from the first diameter 16 to the second diameter 20.

Figure 2:
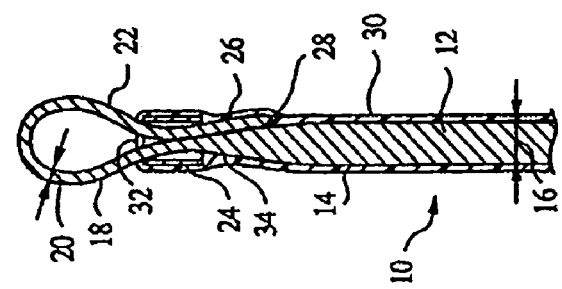
FIG. 2 is a side view of a wire guide according to a second embodiment of the invention.
Figure 3:
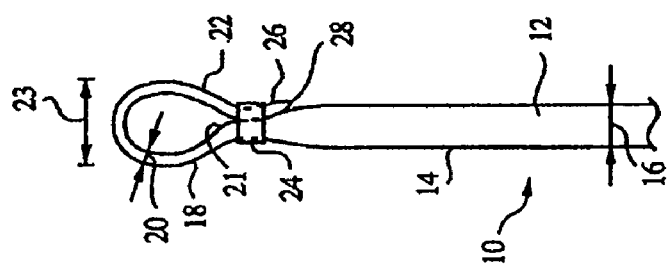
FIG. 3 is a side view of a wire guide according to a third embodiment of the invention.

The elongate member 12 defines a loop 22. In the presently preferred embodiment, the loop 22 comprises a section of the elongate member 12 bent back upon itself. As illustrated in FIGS. 1 and 2, the second portion 18 preferably defines the entire loop 22. Alternatively, as illustrated in FIG. 3, the second portion 18 can defines only a portion of the loop 22. In this embodiment, the intermediate portion 21 preferably defines at least a portion of the loop 22.

Preferably, as illustrated in the figure, the loop 22 comprises a curvilinear loop forming a generally ovoid shape. Also preferable, the loop 22 has a loop width 23 that is greater than the first diameter 16 of the first portion 14 of the elongate member 12. The term 'loop width' refers to the distance between the two outer most surfaces of the elongate member 12 at the widest portion of the loop 22.

The elongate member 12 has a distal end 26 and a distal tip 28. Preferably, the distal tip 28 tapers from the second diameter 20 to a smaller diameter, and particularly preferably tapers to a point. As illustrated in FIG. 1, the loop 22 is preferably formed in a manner that positions the distal end 26 adjacent the intermediate portion 21. Preferably, this placement also positions the distal tip 28 adjacent the intermediate portion 21. Such placements provide a low profile over the portion of the elongate member 12 that has a double width (i.e., two sections of the elongate member 12). Alternatively, as illustrated in FIG. 2, the loop 22 can be formed such that the distal end 26 is positioned adjacent the second portion 18 of the elongate member 12.

Figure 7:
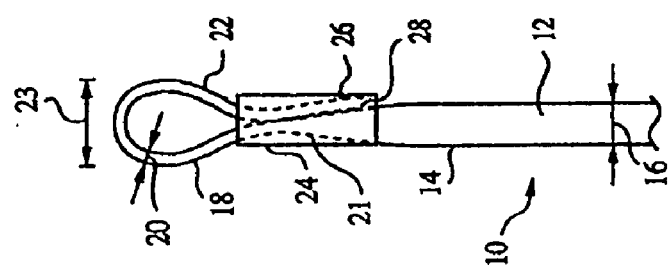
FIG. 7 is a side view of a wire guide according to a fifth embodiment of the invention.

Any method of forming loop 22 is contemplated. In one preferred embodiment, a closure member 24 closes the loop 22 such that no opening exists to the interior space of the loop 22. As illustrated in FIG. 1, the closure member 24 preferably positions the distal end 26 adjacent another portion of the elongate member 12. Any suitable closure member can be used, including bonds, adhesives, and separate members. Examples of suitable closure members include sutures or other appropriate material tying the two sections together, adhesive bonds and other bonds (such as a solder bond, a welded bond, or a molded bond) and a connector (such as a rivet). As best illustrated in FIGS. 1 and 7, the closure member 24 preferably is a cannula defining an interior lumen. Two sections of the elongate member are positioned within the cannula to form the loop 22. As shown in FIG. 7, the cannula preferably extends over and covers the distal end 26 and distal tip 28. Preferably, the closure member 24 is tightened, such as by crimping, to fix the loop 22 in overall size.

Figure 10:
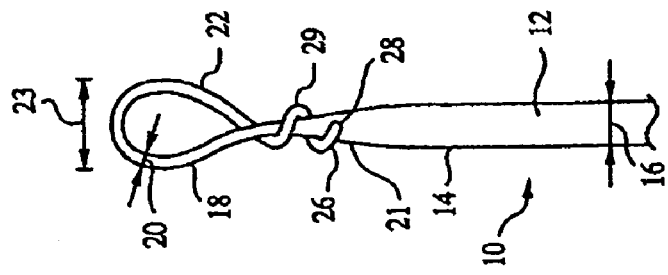
FIG. 10 is a side view of a wire guide according to an eighth embodiment of the invention.
Figure 9:
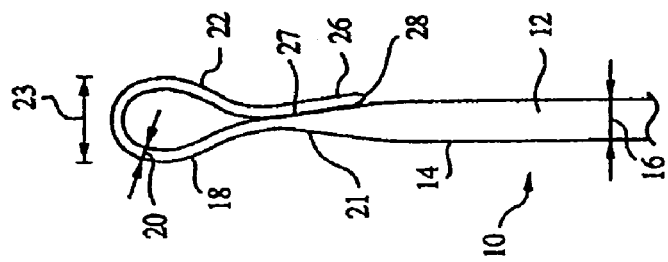
FIG. 9 is a side view of a wire guide according to a seventh embodiment of the invention.
Figure 8:
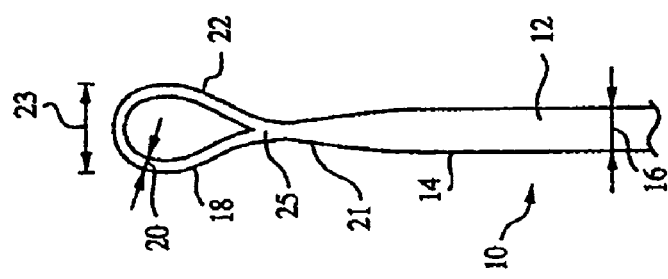
FIG. 8 is a side view of a wire guide according to sixth embodiment of the invention.

In the alternate preferred embodiment shown in FIG. 8, the loop 22 of wire guide 10 is formed by molding two sections of the elongate member together. In another alternate preferred embodiment shown in FIG. 9, two sections of the elongate member are welded or soldered together to form loop 22. In the alternate preferred embodiments shown in FIGS. 10-12, the loop 22 of wire guide 10 is formed from a coiled wire. More specifically, two sections of the elongate member are wound about each other. Preferably, the distal end 26 is wound such that a low profile is achieved. In yet another alternate preferred embodiment (not shown), the loop 22 and elongate member 12 of wire guide 10 may be formed using laser cutting techniques as are known to those skilled in the art. In still another alternate embodiment shown in FIGS. 13-15, the closure member 24 comprises at least one attachment tab 25, which is bent about a portion of the elongate member 12. Optionally, the at least one attachment tab 25 can also be bonded to the elongate member 12 via any method known in the art including, but not limited to, solder, welded or adhesive bonded.

Any suitable material can be used for the elongate member 12, and a variety of suitable materials are known to those skilled in the art. The material chosen need only be biocompatible and able to be formed into the structures described herein. Examples of suitable materials include stainless steel and nitinol. The elongate member 12 may comprise a wire, a tubular member or a sheet of material. Further, the elongate member 12 can be formed of a series of layers, or as a coated core structure. For example, in one embodiment, the elongate member 12 comprises a Nitinol™ core with a polytetrafluoroethylene covering.

The closure member 24 can be formed of any suitable material, and need only be biocompatible and capable of maintaining the loop 22 in a closed position. Preferably, the closure member 24 comprises attachment tabs 25 formed of stainless steel or Nitinol™. Also preferable, the closure member 24 is able to maintain a tightened position on the elongate member 12 upon application of a suitable force, such as by applying a crimping workload to the closure member 24.

A variety of shapes and sizes of elongate members and loops can be used, and these can both be optimized based on particular applications. The dimensions of the elongate member 12 and loop 22 will depend upon various factors, including the intended use of the wire guide and the vessels into which the wire guide will be positioned. For a wire guide intended to cannulate the common bile duct, suitable dimensions include a first diameter 16 of between approximately 0.016 inches and approximately 0.038 inches, and preferably comprises a diameter of approximately 0.035 inches. The second diameter 20 of the wire guide preferably has a diameter of between approximately 0.003 inches and approximately 0.010 inches, and preferably comprises a diameter of approximately 0.006 inches. The intermediate portion of this wire guide defines a taper between the first diameter 16 and the second diameter 20. The taper may be smaller or approximately the same size as the second diameter 20. Preferably, the intermediate portion defines a taper from approximately 0.006 inches to approximately 0.016 inches. For this wire guide, the loop is preferably ovoid in shape with a length of between approximately 4 and approximately 5 millimeters, and a width of between approximately 2 and approximately 3 millimeters.

Figure 4:
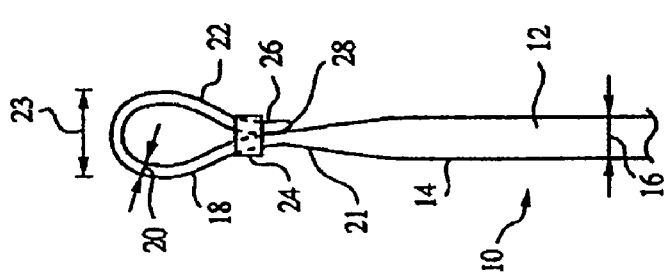
FIG. 4 is an elongate cross-sectional view of a wire guide according to a fourth embodiment of the invention.

FIG. 4 illustrates a wire guide 10 according to a fourth embodiment of the present invention. In this embodiment, a covering 30 is positioned over the closure member 24. The covering 30 can be polytetrafluoroethylene, or another suitable material. Examples of suitable coverings include fluoropolymers, polyurethanes, and other suitable coatings used in the medical device arts. Also, the covering 30 preferably is positioned over the closure member 24 and at least a section of the first portion 14. Particularly preferable, the covering is positioned over the first 32 and second 34 transition areas between the closure member 24 and the elongate member 12. This positioning of the covering 30 ensures a smooth surface at the transition areas 32, 34.

Alternatively, the covering 30 can comprise a coating on the elongate member 12. The coating is preferably applied to the entire elongate member 12, including the loop 22. Alternatively, the coating can be applied to only a portion of the elongate member. The coating may be applied by dipping, molding, or spraying a suitable coating material, such as polytetrafluoroethylene, urethane, and/or other polymeric coatings, directly to the elongate member 12.

A thin PTFE heat shrinkable material is a preferred coating. The heat shrinkable nature of these materials facilitate manufacturing while providing a lubricious coating, which facilitates navigation. In preferred embodiments, the thickness of the coating is between approximately 0.001 and 0.010 inches. In particularly preferred embodiments, the thickness of the coating is between approximately 0.001 and 0.005 inches. In still more preferred embodiments, the thickness of the coating is between approximately 0.001 and 0.002 inches. These preferred thicknesses provide suitable coatings while not adding significantly to the overall thickness of the device.

Also, the wire guide 10, with or without the covering 30, may be treated with a hydrophilic coating or hybrid polymer mixture, such as those based on polyvinyl puroladine and cellulose esters in organic solvent solutions. These solutions make the wire guide particularly lubricious when in contact with body fluids, which aids in navigation.

Radiopaque materials such as bismuth or gold can be added in the covering 30. Also, radiopaque markers known in the art can be placed on the elongate member 12, the loop 22, and/or the closure member 24. Several examples of suitable radiopaque materials and markers are known in the art, and any suitable material and/or marker can be utilized in the present invention.

As illustrated in the figures, the loop 22 is preferably formed by the elongate member 12. As an alternative, a separate member defining the loop can be affixed to a substantially straight elongate member to form the wire guide of the present invention. This may be advantageous when it is desirable to form the loop and elongate member of different materials. For example, a nylon or silicon loop could be formed and attached, such as by a closure member, to an elongate member formed of nitinol. Such an assembly could be coated and or associated with a covering as described above.

Figure 5:
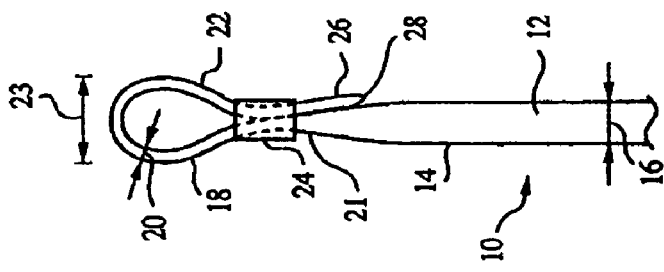
FIG. 5 is a side view illustrating a wire guide according to the present invention encountering an impediment in a body vessel.

FIG. 5 illustrates a wire guide 10 according to the present invention encountering an impediment 42 within a body vessel 40. As illustrated in the figure, the loop 22 deforms in response to its encounter with the impediment 42. Due to the presence of the loop 22 and closure member 24, the distal end 26 does not move relative to the remainder of the elongate member 12. Also, the loop 22 deforms in response to the impediment, enabling the wire guide to continue navigating along the interior of the vessel 40. The resiliency of the loop 22 creates a force opposing the impediment 42 and forces the loop 22 away from the impediment 42, which defines a path for the remainder of the wire guide 10 to follow.

Figure 6:
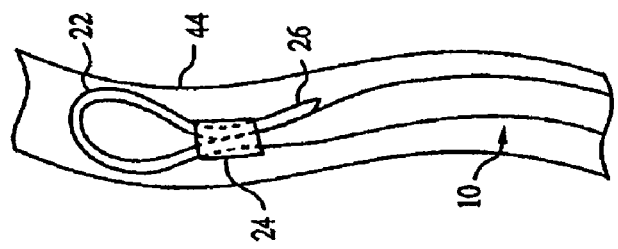
FIG. 6 is a side view illustrating a wire guide according to the present invention encountering a torturous path within a body vessel.

FIG. 6 illustrates a wire guide 10 according to the present invention encountering a torturous path 44 within a body vessel 40. As illustrated in the figure, the loop 22 deforms slightly in response to the torturous path 44. Also, due to the presence of the loop 22 and closure member 24, the distal end 26 does not move relative to the remainder of the elongate member 12. This allows the wire guide 10 to continue navigating along the interior of the body vessel 40. The taper of the intermediate region 21 provides additional flexibility to the wire guide 10, facilitating navigation of the loop 22 through the torturous path 44.

The invention claimed is:

1. A wire guide capable of manipulation about at least one of a tortuous path and an impediment comprising:

an elongate member having a first portion with a first diameter and a second portion with a second diameter, the second diameter being smaller than the first diameter, the second portion of the elongate member being bent back upon itself to form a loop having an interior space, and a closure member for maintaining the loop;

wherein the closure member comprises at least one attachment tab having a base portion integrally formed with the second portion of the elongate member at a first location, and further having an extending portion that wraps about the second portion of the elongate member at a second location that is disposed adjacent to the first location, and wherein the wire guide is configured to be advanced through the lumen of an elongate medical device and guide the elongate medical device about at least one of the tortuous path and the impediment.

2. The wire guide of claim 1, further comprising a covering positioned over at least part of the first portion and the closure member.

3. The wire guide of claim 2, wherein the covering is a heat shrinkable polymeric coating.

4. The wire guide of claim 2, further comprising a radiopaque marker positioned on the covering.

5. The wire guide of claim 1, wherein a hydrophilic polymer coating lubricates an outer surface of the wire guide during navigation through a body lumen.

6. The wire guide of claim 1, wherein the second portion defines the loop.

7. The wire guide of claim 1, wherein the second portion defines only a portion of the loop.

8. The wire guide of claim 1, wherein the loop has a loop width that is greater than the first diameter.

9. The wire guide of claim 1, wherein the elongate member has an intermediate portion between the first portion and the second portion; and wherein the intermediate portion defines a taper from the first diameter to the second diameter.

10. The wire guide of claim 9, wherein the loop is formed by disposing a distal end of the second portion adjacent to the intermediate portion.

11. The wire guide of claim 1, wherein the loop is formed by disposing a distal end of the second portion adjacent to a proximal portion of the second portion.

12. The wire guide of claim 1, further comprising a radiopaque marker positioned on the elongate member.

13. The wire guide of claim 1, further comprising a radiopaque marker positioned on the closure member.

14. The wire guide of claim 1, further comprising a radiopaque marker positioned on the loop.

15. The wire guide of claim 1, wherein the closure member comprises a pair of attachment tabs integrally formed with the second portion of the elongate member at the first location.

16. The wire guide of claim 15, wherein each of the pair of attachment tabs is wrapped about the second portion at the second location.

* * * * *